United States Patent [19]

Wurtman

[11] 4,405,629

[45] Sep. 20, 1983

[54] PROCESS FOR INCREASING GLYCINE LEVELS IN THE BRAIN AND SPINAL CORD

[75] Inventor: Richard J. Wurtman, Waban, Mass.

[73] Assignee: Massachusetts Institute of Technology, Cambridge, Mass.

[21] Appl. No.: 145,644

[22] Filed: May 2, 1980

Related U.S. Application Data

[62] Division of Ser. No. 36,925, May 7, 1979, abandoned.

[51] Int. Cl.³ ................. A61K 31/195; A61K 31/445
[52] U.S. Cl. .................................... 424/267; 424/319
[58] Field of Search ............................... 424/319, 267

[56] References Cited

PUBLICATIONS

Chem. Abst. 75-73544P, (1971).
Chem. Abst. 80-69537Z, (1974).
Chem. Abst. 85-14103C, (1976).
Chem. Abst. 85-74674Z, (1976).

Primary Examiner—Stanley J. Friedman
Attorney, Agent, or Firm—Arthur A. Smith, Jr.; Paul J. Cook

[57] ABSTRACT

The level of glycine in the brain and in the spinal cord is regulated by administering a neutral amino acid composition to a human wherein increased or decreased brain and spinal cord levels of glycine is effected when the composition contains increased or decreased amounts of threonine or a precursor of L-threonine. The neutral amino acid composition can be administered alone or concomitantly with a drug which either has the undesirable side effect of suppressing glycine-mediated neurotransmission or whose therapeutic efficacy is enhanced by increasing glycinergic neurotransmission.

4 Claims, No Drawings

PROCESS FOR INCREASING GLYCINE LEVELS IN THE BRAIN AND SPINAL CORD

The Government has rights in this invention pursuant to Grant Number AM-14228 awarded by the National Institute of Health.

This is a division, of application Ser. No. 036,925 filed May 7, 1979, now abandoned.

BACKGROUND OF THE INVENTION

This invention relates to a method and composition for regulating (increasing and decreasing) the level of glycine in the brain and in the spinal cord.

Prior to the present invention, it was thought that glycine was formed in vivo, in the mammalian central nervous system, from serine by the removal of a hydroxyl group. It had also been proposed that glycine could be produced in vivo by the aldol cleavage of threonine to yield glycine and acetaldehyde, Meltzer et al, J. Biol. Chem., 107, pp 461–474 (1952). In order to test this hypothesis, experiments were conducted with chicks that were fed a diet containing L-threonine to determine the effect of L-threonine on glycine formation in vivo. As reported by D'Me lo at Nutr. Metabol., 15, pp 357–363 (1973), L-threonine was found to have no appreciable influence on plasma glycine levels. Accordingly, it was concluded that threonine is not readily degraded to glycine and that it cannot act as a precursor of glycine.

Glycine is known to be an inhibitory neurotransmitter in the brain and, especially, the spinal cord. Prior to the present invention, there are no drugs or other treatments for increasing the amount of glycine present in synapses. It is known that conditions or treatments that decrease neuronal glycine levels such as spinal cord lesions or that block glycine's interactions with its receptors such as the poison strychnine cause spasticity and hyper-reflexia. Brain glycine levels also are depressed when animals receive anti-psychotic drugs chronically and glycine-mediated neurotransmission may be involved in the actions of some tranquillizing drugs (like the benzodiazopines).

It would be highly desirable to provide a means for increasing or decreasing the amounts of glycine in the brain and in the spinal cord. Furthermore, it would be desirable to provide such a means which is biochemically specific and which lacks the undesirable side effects of anti-spasticity drugs (such as mephenesin analogs, that cause jaundice, nystagmus, and nausea; or dantrolene, which produces weakness). Such a means would be useful in conditions associated with spasticity such as backache or muscle strain. In addition, such means could be utilized in conjunction with anti-psychotic drugs that have the undesirable side effect of lowering brain glycine levels, or with tranquillizing drugs that act as glycine receptors.

SUMMARY OF THE INVENTION

The present invention provide a method and composition for treating diseases associated with deficiency of glycine in the brain or spinal cord. This invention is based upon the discovery that the administration of L-threonine, an essential dietary amino acid, causes increased glycine levels in the brain and the spinal cord. The L-threonine can be administered alone or in admixture with other amino acids; as the acid, its salts, or as a small peptide; with or without drugs, in order to raise brain and spinal cord glycine levels, and, thereby, to treat diseases associated with deficiency of glycine in the brain or spinal cord. By varying the proportion of tryptophan, another amino acid, in the mixture, the synthesis and synaptic release of serotonin, another brain neurotransmitter, can similarly be controlled. In addition, by varying the proportion of tyrosine, another amino acid, the release of dopamine and/or norepinephrine into neuronal synapses can be controlled. Increased intrasynaptic dopamine levels are obtained after tryosine administration only when the dopamine-releasing neurons are active, i.e., are firing frequently. Increased synaptic norepinephrine levels are obtained by giving tyrosine regardless of whether the norepinephrine-releasing neurons are or are not especially active. Decreases in dopamine and norepinephrine release into synapses can be obtained by lowering brain tyrosine levels by administering neutral amino acid compositions low in tyrosine levels. Decreases in serotonin release can similarly be obtained by lowering brain tryptophan levels. Phenylalanine can, in low doses, be used in place of tyrosine. Glycine synthesis can also be decreased by administering meutral amino acid mixtures that lack threonine and which thus reduce threonine levels in the central nervous system.

DETAILED DESCRIPTION OF SPECIFIC EMBODIMENTS

In accordance with this invention, L-threonine is administered to a patient either alone or in combination with one or more drugs thereby to increase the levels of glycine in the brain and spinal cord. Serotonin release also can be controlled at the same time by varying the proportion of tryptophan present in the amino acid mixture. Dopamine and/or norepinephrine release into synapses also can be controlled by varying the proportion of tyrosine and/or its precursor phenylalanine in the L-threonine-containing composition. In order to increase dopamine release, it is necessary that the dopamine-releasing neurons in the patient's brain be relatively active, i.e., are firing frequently, such as is the case in patients with Parkinson's Disease. However, release of norepinephrine or serotonin into synapses can be varied using amino acid mixtures whether or not the norepinephrine-releasing or serotonin-releasing neurons are especially active. Glycine synthesis and release can be diminished by administering neutral amino acids other than threonine, since such compounds reduce brain and spinal cord threonine levels by competing with it for uptake at the bloodbrain barrier.

The composition of the amino acid mixture that is utilized depends upon the nature of the illness in the patient that is to be treated. When there is need to increase glycine release without increasing that of serotonin, dopamine or norepinephrine, L-threonine is administered, not including serotonin's precursor, tryptophan or the precursors of dopamine or norepinephrine, in doses ranging between 5 mg/kg and 200 mg/kg body weight. This therapy is useful, alone or as an adjunct to drug therapies, in treating muscle spasticity, (e.g., in paraplegia, multiple sclorosis, or vertabrae disc abnormalities), certain types of tremor, muscle cramps, or certain conditions requiring a tranquilizer. When there is a need to increase dopamine and/or norepinephrine released into neuronal synapses, tyrosine is included in the L-threonine composition in amounts generally between about 2.5 and 100 mg/kg body weight. In some situations, phenylalanine can be used as a substitute for tyrosine, inasmuch as much of this amino acid is converted to tyrosine in the liver, and released into the blood stream for uptake into the brain. However, plasma phenylalanine levels should be less than about double those of tyrosine, since at the higher levels, phenylalanine competes with tyrosine for uptake into the brain, and can inhibit the enzyme tyrosine hydroxylase.

When there is need to sustain or increase brain serotonin levels while increasing glycine release, these compositions also contain tryptophan. This combination is especially useful in treating certain types of depression, or sleep disorders. Generally, the tryptophan is utilized in these compositions in amount of between about 2.5 and 100 mg/kg body weight.

When there is need to decrease glycine release (by decreasing the availablity of threonine in the brain or spinal cord), such other neutral amino acids as leucine, isoleucine, valine, tyrosine, phenylalanine, or tryptophan are given, in combined amounts of 10 mg/kg to 50 mg/kg, without threonine. This treatment is useful in conditions associated with muscular flaccidity.

The L-threonine, tyrosine, phenylalanine or tryptophan, or other amino acids can be administered as free amino acids, esters, salts, natural or synthetic polymers or as constituents of foods. The route of administration can be oral or parenteral, e.g., intravenous. The L-threonine can be administered with drugs in order to increase glycine levels in the brain and spinal cord during drug treatment. The drugs utilized in the compositions of this invention with L-threonine can have the effect of either lowering or raising glycine levels in the brain or spinal column. In the first instance, the L-threonine corrects the glycine deficiency caused by the drug. In the latter instance, the L-threonine increases the effectiveness of the drug's action of enhancing glycinergic neurotransmission so that it is thereby possible to reduce the dosage of the drug. For example, L-threonine can be administered with haloperidol or thorazine (which lower glycine levels) to treat psychosis, with mephenesin analogs or dantrolene to treat muscle spasticity, with benzodiazepines to attain tranquillization, etc.

The following examples illustrate the present invention and are not intended to limit the same.

EXAMPLE I

This example illustrates that levels of glycine in the brain and spinal cord can be increased by administering L-threonine to an animal.

Male Sprague-Dawley rats (Charles River Breeding Laboratories, Wilmington, MA) weighing 150–175 g were given ad libitum access to tap water and a formula diet and Charles River rat maintenance maintained under light for twelve hours per day. The rats were given L-threonine dissolved in saline intraperitoneally at the levels set forth in Table I. One hour after administration, the rats were killed. The brains and spinal cords were removed, frozen on dry ice and subsequently homogenized. The glycine (GLY) and threonine (THR) contents of the homogenates were assayed using a Beckmann amino acid autoanalyzer.

L-threonine (Grand Island Biological Co., Long Island, N.Y.) which is poorly soluble in water was dissolved in dilute NaOH; the solution was then buffered to pH 7.4 with hydrochloric acid and brought to a known volume with saline. This yielded a fine suspension that was suitable for injection.

The results are set forth in Tables I and II.

TABLE I

| Dose of Threonine (mg/kg) | Brains | |
|---|---|---|
| | THR | GLY |
| | (micromoles per gram ± SEM) | |
| Control | .27 ± .02 | .50 ± .09 |
| 50 | .41 ± .09 | .55 ± .11 |
| 100 | .47 ± .02 | .63 ± .05 |
| 200 | .54 ± .05 | .64 ± .08 |
| 400 | .65 ± .02 | .62 ± .04 |

TABLE II

| Dose of Threonine (mg/kg) | Spinal Cords | |
|---|---|---|
| | THR | GLY |
| | (micromoles per gram + SEM) | |
| Control | 2.6 ± .04 | .49 ± .04 |
| 50 | 2.6 ± .11 | .56 ± .04 |
| 100 | 3.1 ± .16 | .67 ± .04 |
| 200 | 3.1 ± .07 | .80 ± .04 |
| 400 | 3.3 ± .10 | 1.09 ± .04 |

As shown in Tables I and II brain and spinal cord levels of glycine, as a result of L-threonine administration, a much greater effect is seen in spinal cords than in brains. This is compatible with the known distribution of glycine-releasing neurons.

I claim:

1. The process for increasing the amount of glycine in the brain and spinal cord of a patient undergoing haloperidol therapy and suffering from a natural or unduced deficiency of glycine in the brain or spinal cord which comprises administering to said patient an effective amount of a neutral amino acid composition comprising L-threonine, a prcursor of L-threine or mixtures thereof.

2. A composition of matter in unit dosage form comprising haloperidol and a neutral amino acid composition containing L-threonine in an amount sufficient to effect an increase in glycine levels in the brain or spinal cord when administered to a patient.

3. The composition of claim 2 which includes tyrosine, phenylalanine or mixtures thereof in an amount sufficient to increase dopamine and/or norepinephrine released into synapses.

4. The composition of claim 2 which includes tryptophan in an amount sufficient to increase brain serotonin levels.

* * * * *